United States Patent
Wakamatsu

(10) Patent No.: US 8,029,741 B2
(45) Date of Patent: Oct. 4, 2011

(54) SENSING DEVICE

(75) Inventor: Shunichi Wakamatsu, Saitama (JP)

(73) Assignee: Nihon Dempa Kogyo Co., Ltd. (JP)

( * ) Notice: Subject to any disclaimer, the term of this patent is extended or adjusted under 35 U.S.C. 154(b) by 252 days.

(21) Appl. No.: 12/159,139

(22) PCT Filed: Dec. 27, 2006

(86) PCT No.: PCT/JP2006/326375
§ 371 (c)(1),
(2), (4) Date: Nov. 18, 2009

(87) PCT Pub. No.: WO2007/077963
PCT Pub. Date: Jul. 12, 2007

(65) Prior Publication Data
US 2010/0061893 A1 Mar. 11, 2010

(30) Foreign Application Priority Data
Dec. 28, 2005 (JP) .................................. 2005-379070

(51) Int. Cl.
G01N 33/00 (2006.01)
(52) U.S. Cl. ...................... 422/403; 422/420; 422/68.1
(58) Field of Classification Search .................. 422/403, 422/420, 68.1
See application file for complete search history.

(56) References Cited

FOREIGN PATENT DOCUMENTS

| JP | 2002048797 | 2/2002 |
|----|------------|--------|
| JP | 2003315254 | 11/2003 |
| JP | 2004047929 | 2/2004 |
| JP | 2004069377 | 3/2004 |
| JP | 2005114697 | 4/2005 |

OTHER PUBLICATIONS

English Abstract of JP 2002-048797.
English Abstract of JP 2004-047929.
English Abstract of JP 2003-315254.
English Abstract of JP 2005-114697.
English Abstract of JP 2004-069377.
Japanese Office Action with English translation of reasons for rejection.

Primary Examiner — Sam P Siefke
(74) Attorney, Agent, or Firm — Andrus, Sceales, Starke & Sawall, LLP

(57) ABSTRACT

An object of the present invention is to provide a sensing device capable of easily grasping whether or not a concentration of a sensing target is equal to or less than a standard value. As a concrete means for solving the problem, a sensing device which senses, using a piezoelectric vibrator provided with an adsorbing layer for adsorbing a sensing target and electrodes, and having a natural frequency varied by an absorption of the sensing target, the sensing target by the variation of the natural frequency of the piezoelectric vibrator, is structured to include an oscillation circuit for oscillating the piezoelectric vibrator, a measuring section for measuring a concentration of the sensing target based on an oscillation output from the oscillation circuit, a storage section for storing data in which a plurality of sensing targets and their standard concentrations are corresponded to each other, a selecting unit for selecting the sensing target, a data processing section for reading out the standard concentration corresponding to the sensing target selected by the selecting unit from the storage section and comparing the standard concentration with a concentration detection value detected by the measuring section, and an output section for outputting a comparison result compared by the data processing section.

5 Claims, 8 Drawing Sheets

SENSING DEVICE

TECHNICAL FIELD

The present invention relates to a sensing device which senses, using a piezoelectric vibrator provided with an adsorbing layer for adsorbing a sensing target and electrodes, and having a natural frequency varied by an absorption of the sensing target, the sensing target by the variation of the natural frequency of the piezoelectric vibrator.

BACKGROUND ART

In order to quantify the mass and concentration of a sensing target which is included in a very small amount in an environment or in a living body such as, for instance, an environmental pollutant like dioxin, PCB (polychlorinated biphenyl), and the like, contained in a river, various antibiotics used for raising fishes and are remained in the blood of the raised fishes, and diseased substances such as prion which causes BSE (bovine spongiform encephalopathy) in an animal body tissue, there is known a sensing device using a crystal sensor being a sensing sensor provided with a crystal vibrator having, for instance, a crystal piece as a piezoelectric piece, in which an excitation electrode for exciting the crystal piece is respectively provided to one surface side and the other surface side of the crystal piece.

If explained more in detail regarding this sensing device, the sensing device includes, other than the above-described crystal sensor, for example, a frequency measuring device being electrically connected to the crystal sensor and having a frequency detecting section for detecting a frequency generated by the crystal piece, and a PC (personal computer) being electrically connected to the frequency measuring device and having a monitor, or the like, as an output section, for example. Further, at one surface side of the crystal vibrator, an absorbing layer having, for instance, an antibody adhered to the surface thereof is provided, in which the antibody is designed to selectively absorb one of the sensing target such as mentioned above, for example, by an antigen-antibody reaction, and when the sensing target is absorbed in the absorbing layer, the frequency of the crystal piece varies in accordance with the absorption amount of the sensing target. In the above-described PC, a software which analyzes the frequency variation detected by the frequency detecting section of the frequency measuring device and graphically displays the frequency variation on the monitor, for example, is installed.

With the use of thus structured sensing device, when, for example, a user drops a sample solution containing the sensing target on the crystal vibrator after dropping a solvent, the sensing target is absorbed in the absorbing layer, an oscillation frequency of the crystal vibrator decreases in accordance with the absorption amount, and the frequency variation is graphically displayed on the monitor. The user can determine the mass and concentration of the sensing target included in the sample solution by reading the frequency variation amount from the graph and by performing a predetermined calculation based on the variation amount.

Meanwhile, in order to secure the safety of the human body, in an environmental field, there is a case in which a sample solution is prepared by, for example, adding a solvent under a predetermined atmosphere to water collected as a specimen, or by making the air collected as a specimen dissolved in a solvent, and by comparing concentrations of the respective environmental contaminants such as, for instance, the aforementioned dioxin and PCB included in the sample solution, with standard concentrations (tolerance amount) being previously set for each of the various environmental contaminants, for example, to thereby determine the largeness or smallness of these concentrations. Further, also in a food sanitation field, there is a case in which a sample solution is prepared by a specimen such as, for example, the blood of an animal, and by comparing a concentration of a substance toxic to the human body such as various antibiotics included in the sample solution with a standard concentration being previously set for each of the toxic substances, for instance, to thereby determine the largeness or smallness of these concentrations. The aforementioned conventional sensing device can also be applied for performing such determinations, but, in such a case, the user has to perform, other than the aforementioned quantification using the sensing device, an examination and a storage of a standard concentration of the quantified substance, and thereafter, the user compares the standard concentration with the quantified value obtained by the sensing device by matching them with each other, to thereby determine the largeness or smallness of the concentrations, which becomes a great burden on the user when performing determinations with respect to a plurality of sensing targets, for instance.

Note that although a sensing device provided with a crystal sensor is described in Patent Document 1, an aim thereof is to enhance the sensitivity by connecting various components included in the device without using any cables, so that the above-described problems cannot be solved with it.

Patent Document 1

Japanese Patent Application Laid-open No. 2001-083154 (Paragraph 0007, FIG. 1)

DISCLOSURE OF THE INVENTION

A task of the present invention is to eliminate the above-described problems of prior art, and an object of the present invention is to provide a sensing device which enables a user to easily grasp whether or not a concentration of a sensing target is equal to or less than a standard value.

A sensing device of the present invention which senses, using a piezoelectric vibrator provided with an adsorbing layer for adsorbing a sensing target and electrodes, and having a natural frequency varied by an absorption of the sensing target, the sensing target by the variation of the natural frequency of the piezoelectric vibrator, includes: an oscillation circuit for oscillating the piezoelectric vibrator; a measuring section for measuring a concentration of the sensing target based on an oscillation output from the oscillation circuit; a storage section for storing data in which a plurality of sensing targets and their standard concentrations are corresponded to each other; a selecting unit for selecting the sensing target; a data processing section for reading out the standard concentration corresponding to the sensing target selected by the selecting unit from the storage section and comparing the standard concentration with a concentration detection value detected by the measuring section; and an output section for outputting a comparison result compared by the data processing section. Here, the selecting unit may be an input section with which the standard concentration in the storage section is selected by designating the sensing target.

A sensing device of another invention which senses, using a piezoelectric vibrator provided with an adsorbing layer for adsorbing a sensing target and electrodes, and having a natural frequency varied by an absorption of the sensing target, the sensing target by the variation of the natural frequency of the piezoelectric vibrator, includes: a piezoelectric sensor having the piezoelectric vibrator and terminal portions electrically connected to the electrodes of the piezoelectric vibrator; an oscillation circuit for oscillating the piezoelectric vibrator; a measuring section for measuring a concentration of the sensing target based on an oscillation output from the oscillation circuit; a storage section for storing data in which a plurality of sensing targets and their standard concentrations are corresponded to each other; a selecting unit for selecting the sensing target; a data processing section for reading out the standard concentration corresponding to the sensing target selected by the selecting unit from the storage section and comparing the standard concentration with a concentration detection value detected by the measuring section; a main body to which the terminal portions of the piezoelectric sensor are attachably/detachably connected and including the oscillation circuit, the measuring section and the data processing section; and an output section for outputting a comparison result compared by the data processing section, in which the selecting unit includes an identification code being provided to the piezoelectric sensor and corresponding to the sensing target sensed by the piezoelectric sensor, and a reading unit being provided to the main body and reading the identification code to determine the sensing target. In this case, the reading unit is designed to read the identification code while the piezoelectric sensor is attached to the main body, for instance. The identification code is written in a memory in an integrated circuit element provided on the piezoelectric sensor, for example, or it is structured as, for instance, an optically readable bar code or magnetic data. Further, the piezoelectric sensor may be structured to include a liquid accommodating portion to which a sample solution containing the sensing target is supplied.

Further, the present invention may be structured to include an input section for designating the sensing target, and a unit for notifying, when the identification code designated by the input section is inconsistent with the identification code read by the reading unit, the inconsistency of the identification codes.

In the present invention, the data in which the plurality of sensing targets and their standard concentrations are corresponded to each other is stored in the storage section, the standard concentration corresponding to the sensing target is read out from the data by selecting the sensing target with the selecting unit, and also the comparison result obtained by comparing the standard concentration with the concentration of the sensing target measured by the measuring section is output, so that it is possible to easily grasp whether or not the concentration of the sensing target is equal to or less than the standard concentration.

Further, if it is designed such that the sensing sensor including the piezoelectric vibrator is provided with the identification code corresponding to the sensing target sensed by the sensing sensor, and the identification code is read at a side of the main body to thereby determine the sensing target, the sensing target is automatically selected, so that the operations can be simplified.

BEST MODE FOR CARRYING OUT THE INVENTION

Figure 1:
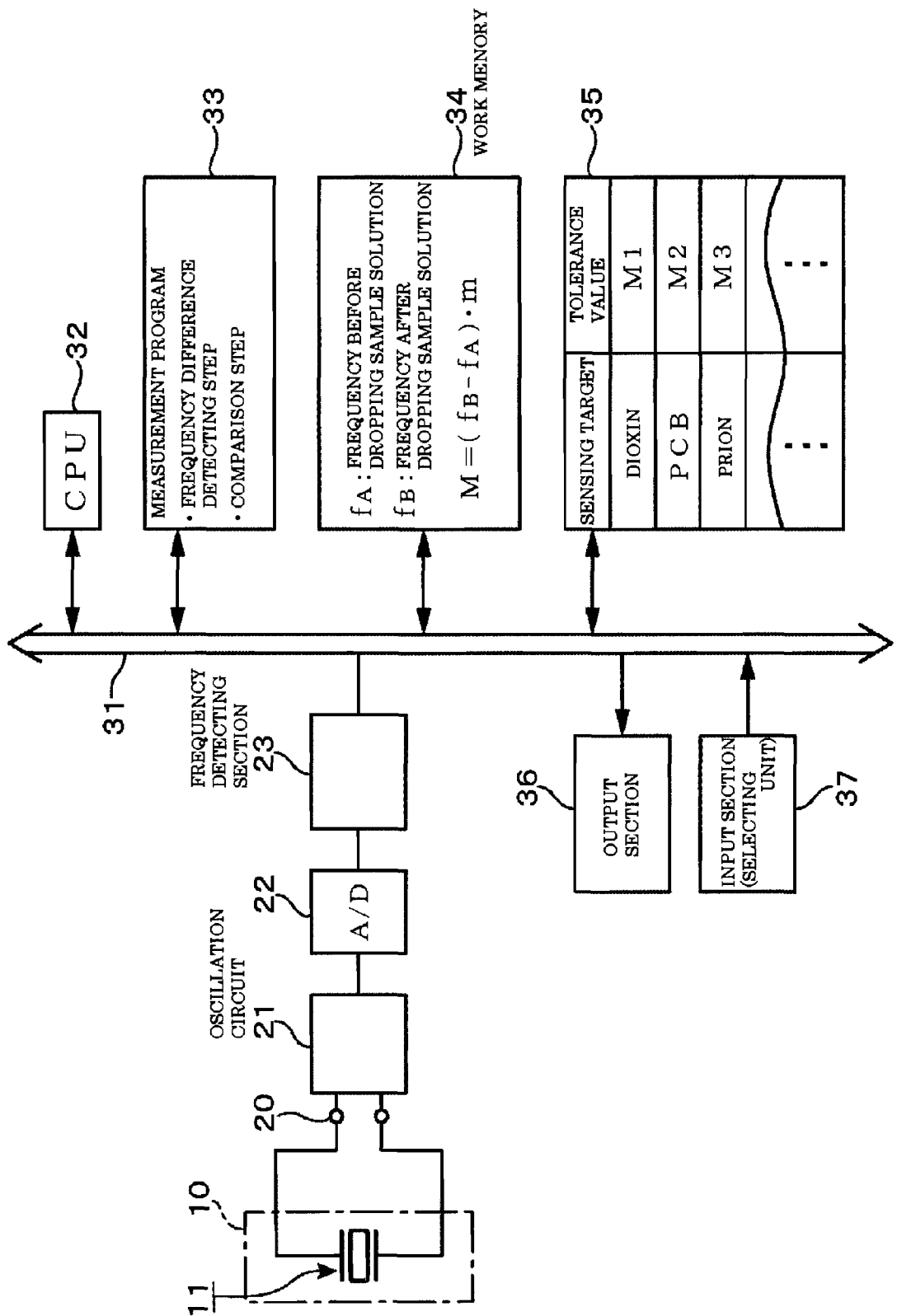
FIG. 1 is a whole structural diagram of a sensing device according to an embodiment of the present invention.

FIG. 1 is a whole structural diagram of one embodiment of a sensing device according to the present invention. "11" in the drawing is a crystal vibrator (piezoelectric vibrator) provided with a crystal piece as a piezoelectric piece. A portion framed by a chain line 10 in the drawing shows a crystal sensor being a piezoelectric sensor (sensing sensor) indicated in the claim, and the crystal vibrator 11 is included therein. "20" in the drawing are terminal portions, which will be described later. The crystal vibrator 11 is connected to an oscillation circuit 21 via the terminal portions 20. At a rear stage of the oscillation circuit 21, an A/D (analog/digital) converter 22 is provided, and at a rear stage of the A/D converter 22, a frequency detecting section 23 is provided. The frequency detecting section 23 is connected to a bus 31. Note that the respective sections located at stages behind the oscillation circuit 21 are included in a main body indicated in the claim.

Next, an explanation will be made regarding respective sections composing the sensing device connected to the bus 31. "32" in the drawing is a CPU (central processing unit) being a calculating section, and "33" in the drawing is a measurement program. This measurement program 33 serves as a frequency difference detecting section and a comparison section, and is structured to execute a frequency difference detecting step for detecting, when an oscillation frequency of the crystal vibrator 11 is varied, the difference in oscillation frequency between before and after the variation of the oscillation frequency, and a comparison step for comparing with a quantified value of a sensing target calculated based on the frequency difference. "34" in the drawing is a work memory being a region for performing a calculation to determine a concentration of the sensing target in a sample solution based on the frequency detected by the frequency detecting section 23.

"35" in the drawing is a data table which stores tolerance values (standard concentration values) corresponding to a plurality of sensing targets such as, for example, dioxin, PCB, and prion. "36" in the drawing is an output section which corresponds to, for instance, a display section composed of a monitor or the like, and a printer. "37" in the drawing is an input section composing a selecting unit, and is formed of, for instance, a keyboard, a mouse, a screen displayed on the display section, and the like. Note that the respective tolerance values can be rewritten to an arbitrary value with the use of the input section 37, for example.

Figure 2:
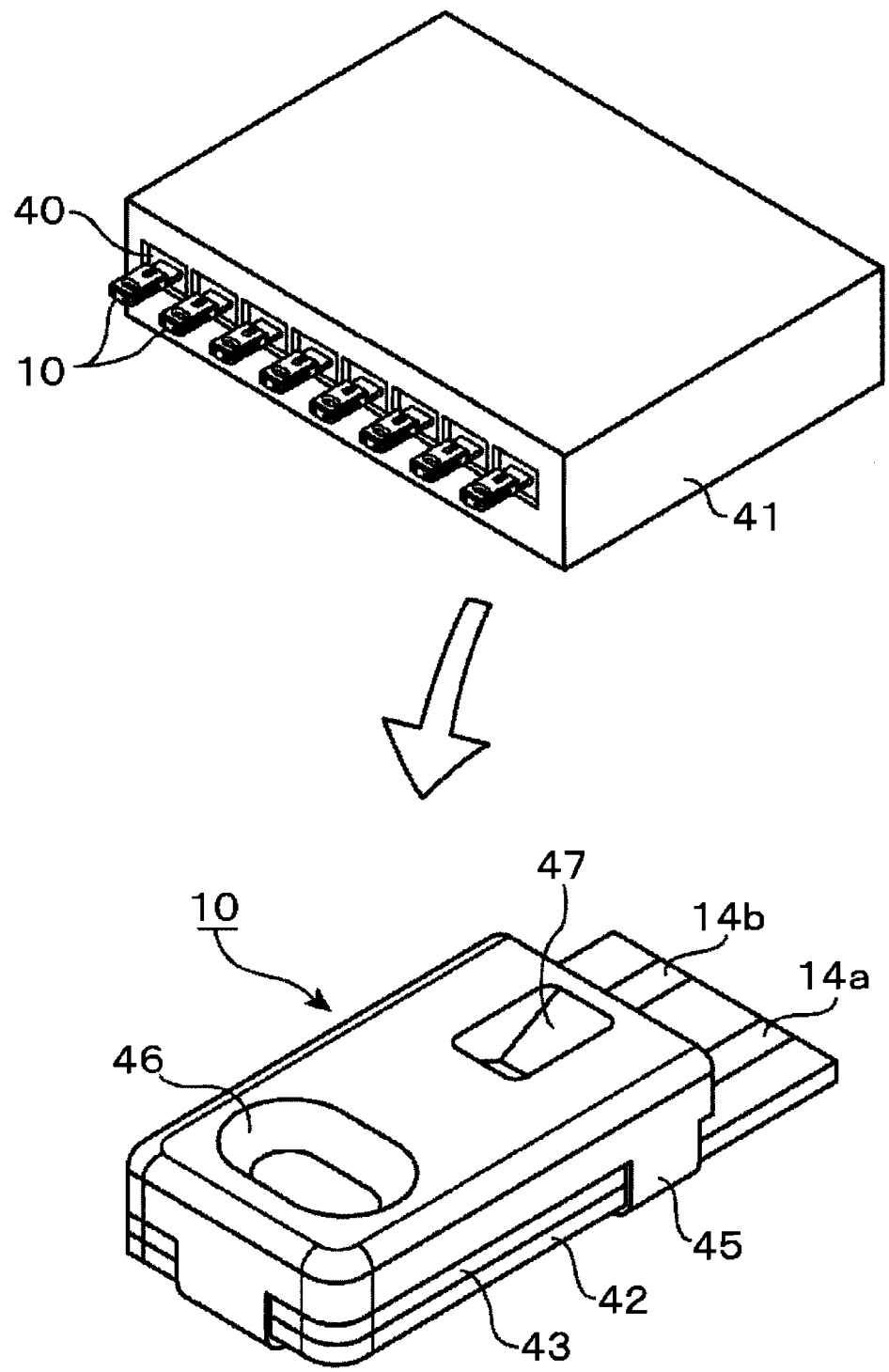
FIG. 2 is an example of a crystal sensor and a frequency measuring device composing the sensing device.

FIG. 2 shows an example of a concrete structure of the respective sections composing the sensing device in FIG. 1. "41" in the drawing is a frequency measuring device, in which the oscillation circuit 21, the A/D converter 22 and the frequency detecting section 23 are included. At a front surface of the frequency measuring device 41, 8 insertion ports 40 are provided, and the crystal sensors 10 of 8 pieces at maximum are respectively attachably/detachably attached to these insertion ports 40. The terminal portions are provided in the insertion port 40, and when the crystal sensor 10 is attached into the insertion port 40, later-described printed circuits 14a and 14b corresponding to terminal portions at a side of the crystal sensor 10 are connected to the aforementioned terminal portions provided in the insertion port 40, and accordingly, the frequency measuring device 41 and the crystal sensor 10 are electrically connected. Note that the terminal portions of the crystal sensor 10 (printed circuits 14a and 14b) and the terminal portions in the insertion port 40 are indicated as the terminal portions 20 in FIG. 1. This sensing device has an 8-channel structure, and when the crystal sensor 10 is electrically connected to the frequency measuring device 41, as described above, the circuit from the crystal vibrator 11 to the A/D converter 22 in FIG. 1 is prepared for 8 channels at maximum, and respective channel outputs are switched and thereby being output to the frequency detecting section 23.

Figure 3:
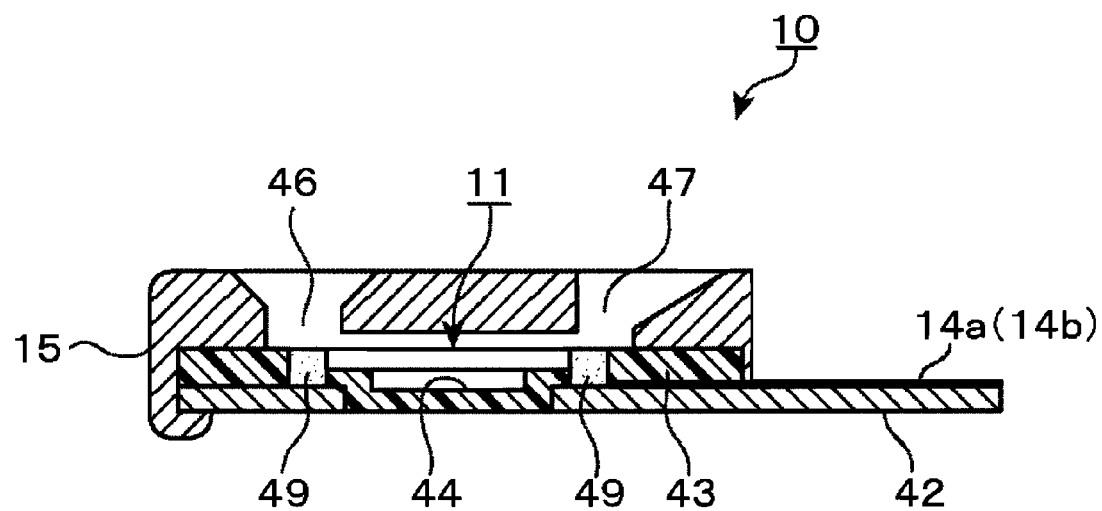
FIG. 3 is a vertical side view of the crystal sensor.

As shown in FIG. 2 and FIG. 3, the crystal sensor 10 is structured such that a rubber sheet 43 is formed over a substrate such as, for instance, a printed-circuit board 42, the crystal vibrator 11 is provided so as to fill a recessed portion 44 formed on the rubber sheet 43, and a top cover case 45 is mounted over the rubber sheet 43. On the top cover case 45, there are formed a fill port 46 through which the sample solution being fluid to be measured is poured, and an observation port 47 for observing the sample solution, in which the sample solution is poured through the fill port 46, and a space at an upper surface side of the crystal vibrator 11 is filled with the sample solution (crystal piece is immersed into the sample solution). In the crystal sensor 10, a portion which is filled with the sample solution corresponds to a liquid accommodating portion. A lower surface side of the crystal vibrator 11 is made to be an air-tight space by the recessed portion 44, to thereby complete the formation of a Languban-typed crystal sensor.

Figure 4:
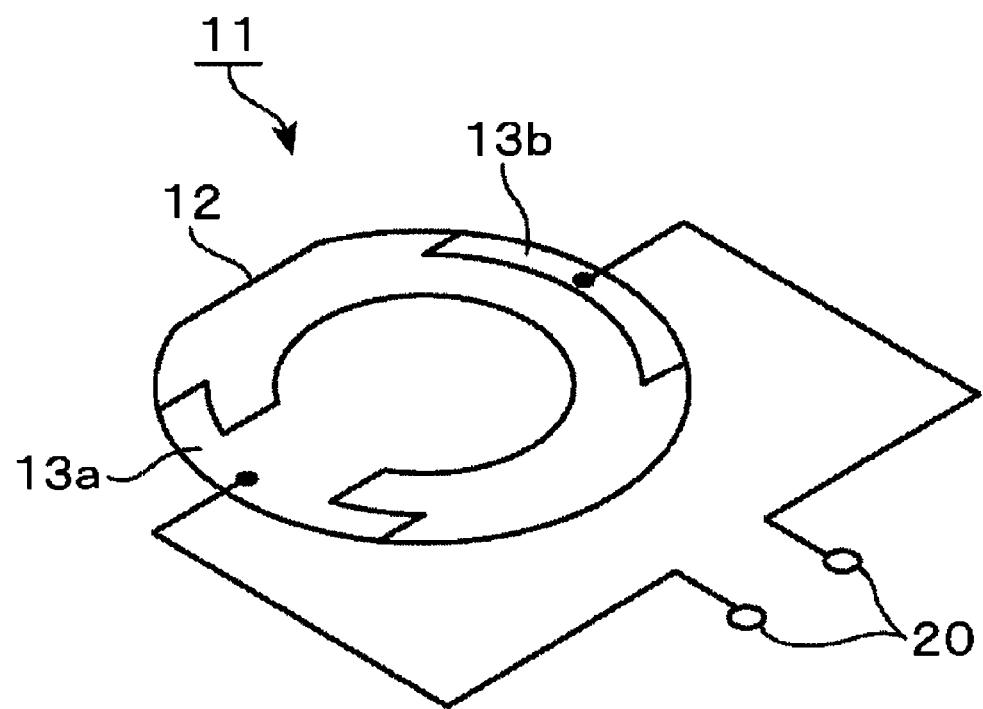
FIG. 4 is an explanatory view showing a crystal vibrator and wiring in the surrounding thereof which compose the crystal sensor.

As shown in FIG. 4, in the crystal vibrator 11, a crystal piece 12 of a circular shape, for instance, is provided at both surfaces thereof with respective electrodes 13a and 13b for oscillating the crystal piece 12, and each having the same shape, for instance (the electrode 13b on a rear surface side is formed serially with a peripheral edge on a front surface side). These electrodes 13a and 13b are respectively electrically connected to the printed circuits 14a and 14b provided on the printed-circuit board 42 via a conductive adhesive 49. Further, at one surface side of the crystal vibrator 11, for instance, at a surface of the circular-shaped portion of the electrode 13a, an absorbing layer (not shown) made of an antibody which selectively absorbs the sensing target (measuring target), for instance, is formed.

Further, although an illustration is omitted, to the frequency measuring device 41, a PC provided with, for instance, a monitor as the output section 36, and a keyboard as the input section 37, respectively, is connected. This PC includes, for example, the CPU 32, the measurement program 33, the work memory 34 and the data table 35, and having an image display software for outputting the comparison result obtained through the measurement program 33 to the monitor being the output section 37, installed therein. Note that, the frequency measuring device 41 and the PC compose the main body indicated in the claim. Further, the frequency detecting section 23, the CPU 32, the measurement program 33 and the work memory 34 compose a measuring section.

Figure 5:
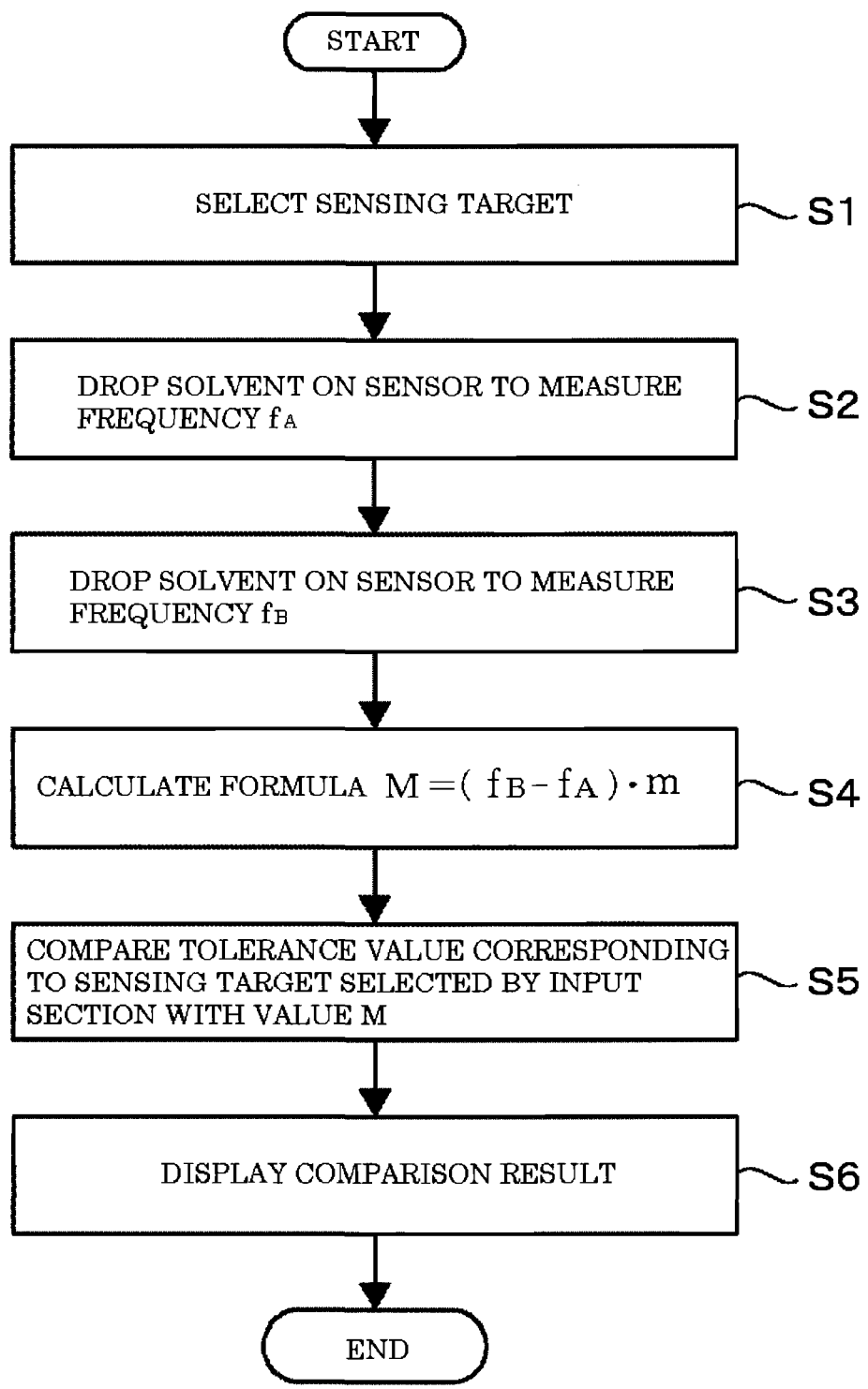
FIG. 5 is a flow chart showing a procedure for performing a determination using the sensing device.

Next, an operation of thus structured sensing device will be explained by referring to FIG. 5 by citing an example where, for instance, a concentration of dioxin in a sample solution prepared from water in a river collected as a specimen is compared with a concentration tolerance value (standard concentration) of dioxin set for the sample solution. For example, by previously collecting a predetermined amount of specimen as a sample, and by diluting the sample using, for example, a solvent including no dioxin is such as pure water, the sample solution is prepared. Note that although the pure water is applied as a solvent for preparing the sample solution in this example, the solvent is appropriately selected in accordance with the sensing target substance or the kind of specimen.

First, dioxin is selected as a sensing target with the use of the keyboard being the input section 37 (step S1). According to this selection, the concentration tolerance value (standard concentration) M1 of dioxin is read out from the data table 35 to be written into the work memory 34.

Subsequently, after attaching a plurality of crystal sensors 10 to the frequency measuring device 41, for instance, in order to determine a blank value of the frequency, the pure water of 2.0 ml, for instance, which is used for preparing the sample solution is poured into one of the fill ports 46 of the crystal sensors 10, to thereby immerse the crystal vibrator 11 into the pure water, and the crystal vibrator 11 is oscillated by the oscillation circuit 21. An oscillation output of the crystal vibrator 11 is input into the frequency detecting section 23, and the frequency is detected. After the oscillation frequency of the crystal vibrator 11 output from the frequency detecting section 23 is stabilized, the measurement program 33 writes the oscillation frequency into the work memory 34 as fA (step S2).

Thereafter, 2.0 ml of a sample solution prepared in the above-described manner is poured into the fill port 46 of the crystal sensor 10 which is different from the one into which the pure water is poured in the step S2, to thereby immerse the crystal vibrator 11 into the sample solution. Subsequently, the oscillation output of the crystal vibrator 11 is input into the frequency detecting section 23, and after the oscillation frequency of the crystal vibrator 11 output from the frequency detecting section 23 is stabilized, the measurement program 33 writes the oscillation frequency into the work memory 34 as fB (step S3). The way of determining the value fB is not limited to this example, and it may be such that the pure water is poured into the crystal sensor 10, and after the pure water in the crystal sensor 10 is discarded, the sample solution is subsequently put into the crystal sensor 10, and a value having the stabilized oscillation output is set as fB, for example. Further, it may be such that the pure water is poured into the crystal sensor 10, and after an oscillation output fA at this time is measured, the sample solution is subsequently put into the crystal sensor 10 without discarding the pure water therein, and a value having the stabilized oscillation output is set as fB, for instance.

The measured frequencies fA and fB are respectively written in the work memory 34, and in the work memory 34, the frequency difference between fA and fB (fA−fB) is calculated by the measurement program 33. The mass of the sensing target absorbed in the absorbing layer is determined by multiplying the frequency difference by a constant, and since the absorption amount corresponds to the concentration of the sensing target in the sample solution, the value (fA−fB) corresponds to the concentration of the sensing target in the sample solution. Therefore, for instance, by previously forming a calibration curve for the respective sensing target and storing it in a separate memory, and also by providing a program for calculating the concentration of the sensing target based on the calibration curve, the concentration of the sensing target is determined when the value (fA−fB) is determined (step S4).

Next, the measurement program 33 compares the tolerance value M1 in the data table 35 read out by the work memory 34 in the step S1 with a is calculated value M calculated in the step S4, to thereby determine whether the tolerance value M1 is larger than the calculated value M, or the tolerance value M1 is smaller than the calculated value M (step S5). By the image display software installed in the PC, when, for example, the tolerance value M1 is larger than the calculated value M, a symbol of "+", for instance, is output to the monitor being the output section 36, and when the tolerance value M1 is smaller than the calculated value M, a symbol of "−", for instance, is output to the monitor (step S6). The way of display can be suitably determined, and it may be displayed by characters, or the like.

According to such an embodiment, the data in which the plurality of sensing targets and their standard concentrations are corresponded to each other is stored in the data table 35, and the standard concentration corresponding to the sensing target is read out from the data by selecting the sensing target with the input section 37. Further, the comparison result obtained by comparing the standard concentration with the concentration of the sensing target calculated by the measurement program 33 based on the variation of the oscillation frequency of the crystal sensor 10 which is caused by the adhesion of the sensing target, is output. Accordingly, it is possible to easily grasp whether or not the concentration of the sensing target is equal to or less than the standard concentration. Therefore, when a user changes the sensing target, for example, there is no need to examine the concentration of the respective sensing targets at every time the sensing target is changed, so that the trouble for the user is reduced.

Figure 6:
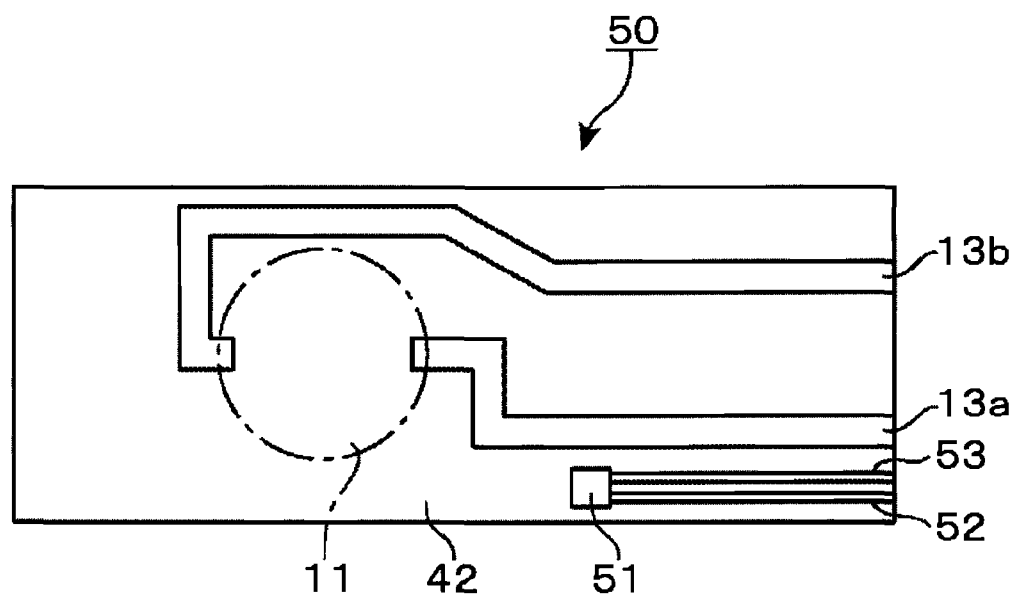
FIG. 6 is an explanatory view showing another embodiment of a crystal sensor.

Next, another embodiment will be explained. FIG. 6 shows a structure of a crystal sensor 50 of this embodiment, and the crystal sensor 50 is structured in substantially the same manner as in the aforementioned crystal sensor 10. However, in FIG. 6, a description regarding the top cover case 45 and the rubber sheet 43 covering the printed-circuit board 42 is omitted. A point where the crystal sensor 50 is different from the crystal sensor 10 is that an IC chip 51 being an integrated circuit element is mounted on the printed-circuit board 42 of the crystal sensor 50, in which a memory on the IC chip 51 includes an identification code corresponding to the kind of the absorbing layer provided to the electrode 13a of the crystal vibrator 11, namely, an identification code corresponding to the sensing target, written therein. "52" and "53" in the drawing are respectively printed circuits composing terminal portions connected to electrodes (not shown) of the IC chip 51.

Figure 7:
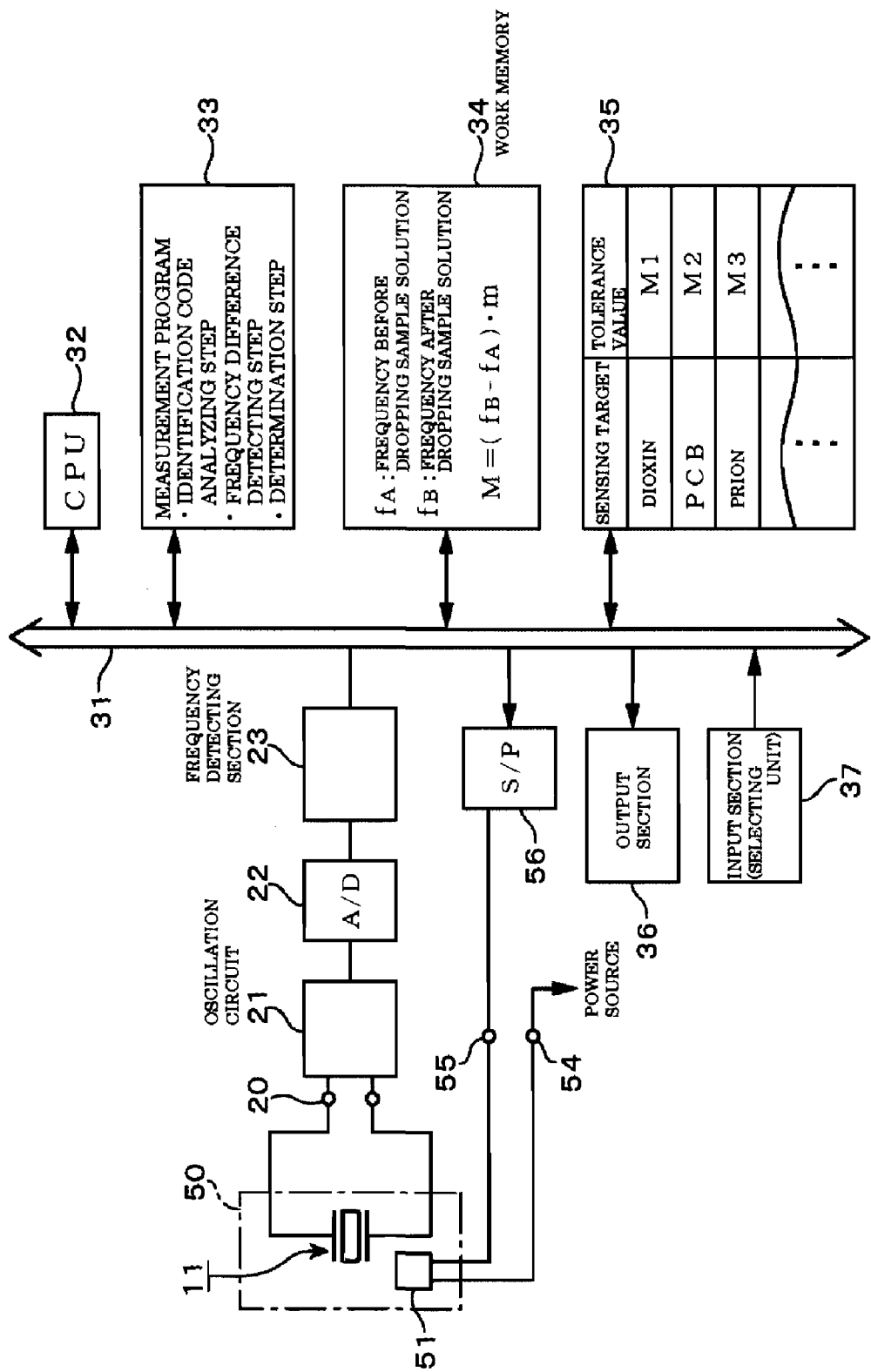
FIG. 7 is a whole structural diagram of a sensing device according to another embodiment of the present invention including the crystal sensor.

FIG. 7 shows an example of a whole structural diagram of a sensing device including such a crystal sensor 50. If explained a point different from the above-described embodiment, in the insertion port 40 of the frequency measuring device 41, for example, terminal portions attachably/detachably connected to the terminal portions of the IC chip 51 (printed circuits 52 and 53) are provided in addition to the terminal portions connected to the printed circuits 14a and 14b, and the terminal portions at the side of the IC chip 51, and the terminal portions in the insertion port 40 connected thereto are indicated as terminal portions 54 and 55 in the drawing. The terminal portion 54 is connected to a power source, and the terminal portion 55 is connected to an S/P (serial/parallel) converter 56 which is shown as "56" in the drawing. Note that the S/P converter 56 is included, for example, in the frequency measuring device 41, and is connected to the bus 31. As same as in the case of the crystal sensor 10, when the printed-circuit board 42 of the crystal sensor 50 is inserted into the insertion port 40 of the frequency measuring device 41, the printed circuits 14a and 14b are connected to the terminal portions corresponding thereto in the insertion port 40, and at the same time, the printed circuits 52 and 53 are also connected to the terminal portions corresponding thereto in the insertion port 40. Further, the measurement program 33 is structured to execute, other than the frequency difference detecting step and the determination step in the above-described embodiment, an ID analyzing step such as explained in an operation of the sensing device.

Figure 8:
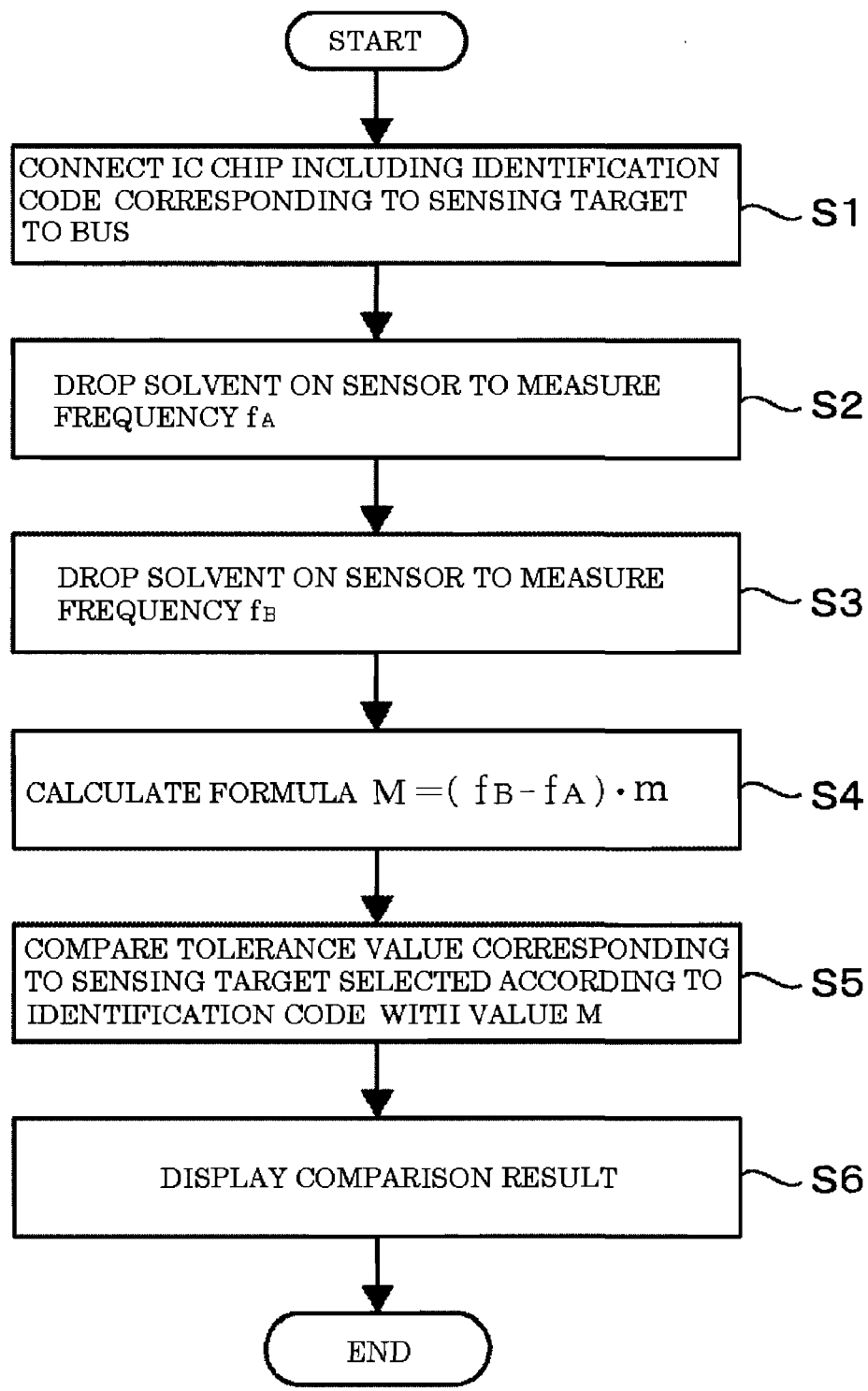
FIG. 8 is a flow chart showing a procedure for performing a determination using the sensing device.

The operation of the sensing device will be explained by referring to FIG. 8. The sensing target is dioxin, as same as in the above-described embodiment. First, as step S1, being different from the step S1 in the above-described embodiment, a plurality of crystal sensors 50 are inserted into the insertion ports 40 of the frequency measuring device 41, for example, to thereby connect the printed circuits 14a and 14b to the terminal portion 54, so that the IC chip 51 is connected to the bus 31 via the S/P converter 56 and is also connected to the power source. According to the connections, the measurement program 33 reads out the identification code stored in the IC chip 51, and the tolerance value corresponding to the identification code, which is, the tolerance value M1 of dioxin in this example, is read out from the data table 35 to be written in the work memory 34. The following steps S2 to S4 are respectively conducted in the same manner as in the steps S2 to S4 in the above-described embodiment. In a step S5 to be performed after that, being different from the above-described embodiment, the magnitude between the tolerance value M1 of dioxin selected in the step S1 based on the identification code and the value M being the concentration value of the sensing target in the sample solution calculated by the step S4, is compared. In the following step S6, as same as in the above-described embodiment, the comparison result obtained in the pre-staged step S5 is output to the output section 36. If the sensing device is thus structured, the sensing target is automatically selected, so that the operations can be simplified.

Further, the aforementioned embodiment may be provided with, instead of the IC chip 51, an identification code such as, for example, a bar code corresponding to the kind of the absorbing layer printed on, for instance, an exposed end portion of the printed-circuit board 42, and an optical reading section for reading the identification code provided to the insertion port 40 of the frequency measuring device 41. In this case, when the crystal sensor is attached to the frequency measuring device 41, the aforementioned reading section reads the identification code on the printed-circuit board 42, and the measurement program 33 analyzes the read identification code. The measurement program 33 may be structured to select the tolerance value in the data table 35 based on the analysis result. Further, the identification code may be magnetic data such as used in a cash card of a bank.

Further, as the output section 36, it is not limited to use the monitor connected to the PC, for instance, and a display section formed of a liquid crystal may be provided to the frequency measuring device 41, for example. Further, the other respective sections such as the CPU 32 included in the PC in the above-described embodiment may also be provided to the frequency measuring device 41, instead of to the PC.

Further, other than the above, an LED (light-emitting diode), an alarm sounder, or the like, for instance, can be applied as the output section 36, and the sensing device may be structured such that, when, for example, the calculated concentration of the sensing target is larger than the tolerance value of the sensing target stored in the data table, the LED is lit up, or an alarm is sounded from the alarm sounder.

Note that in the above-described embodiment in which the tolerance value of the sensing target in the data table 35 is selected based on the identification code in the IC chip 51 or the identification code formed of the bar code, the sensing device may be structured such that the user can select the sensing target with the use of the input section 37, and a program for examining an inconsistency between, for example, the sensing target corresponding to the identification code and the sensing target selected by the input section 37 from the user, is further provided to the PC, and when the inconsistency of the sensing targets is confirmed by the program, characters, symbols, or the like indicating the inconsistency are displayed on the output section 36. By structuring the sensing device as above, it is possible to prevent the crystal sensor 10 from being mistakenly inserted.

The invention claimed is:

1. A sensing device which senses, using a piezoelectric vibrator in which an excitation electrode is respectively formed on one surface side and the other surface side of a crystal piece and an adsorbing layer for adsorbing a sensing target in a sample solution is provided on the excitation electrode of the one surface side, the sensing target being adsorbed by the variation of the natural frequency of the piezoelectric vibrator, said sensing device, comprising:
   (1) a main body having an oscillation circuit for oscillating the piezoelectric vibrator, a measuring section for measuring a concentration of the sending target based on an oscillation output from said oscillation circuit, a storage section for storing data in which a plurality of sensing targets and their standard concentrations are corresponded to each other, a data processing section for reading out the standard concentration corresponding to the sensing target from the storage section and comparing the standard concentration with a concentration detection value detected by the measuring section; and an output section for outputting a comparison result compared by said data processing section;
   (2) a piezoelectric sensor having a substrate on which wirings are formed, the piezoelectric vibrator provided on the substrate in parallel with the substrate and having the excitation electrode on the other surface side thereof provided to face a space divided from an accommodating region for the sample solution, a unit being provided to the substrate and holding an identification code corresponding to the sensing target sensed by the piezoelectric vibrator, terminal portions provided on the substrate and electrically connected to the excitation electrodes of the piezoelectric vibrator via the writings, and a case surrounding a space above the one surface side of the piezoelectric vibrator to form the accommodating region for the sample solution which is brought into contact with the absorbing layer, and having a fill port for the sample solution formed on an upper surface thereof, and is structured to enable the terminal portions to be connected to terminals on a side of said main body by inserting the substrate into an insertion port of said main body; and
   (3) a reading unit being provided to said main body and reading the identification code of said piezoelectric sensor attached to said main body to determine the sensing target.

2. The sensing device according to claim 1, wherein said selecting unit is an input section with which the standard concentration in said storage section is selected by designating the sensing target.

3. The sensing device according to claim 1, wherein the identification code is written into a memory in an integrated circuit element provided on said piezoelectric sensor.

4. The sensing device according to claim 1, wherein the identification code is magnetic data.

5. The sensing device according to claim 1, wherein the piezoelectric vibrator is positioned above a hole portion formed on the substrate, and a rubber sheet is interposed between the case and the substrate.

* * * * *